United States Patent
Baynham

(10) Patent No.: US 9,730,737 B2
(45) Date of Patent: Aug. 15, 2017

(54) FACET FIXATION WITH ANCHOR WIRE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 37 days.

(21) Appl. No.: 14/214,352

(22) Filed: Mar. 14, 2014

(65) Prior Publication Data

US 2014/0288601 A1 Sep. 25, 2014

Related U.S. Application Data

(60) Provisional application No. 61/785,369, filed on Mar. 14, 2013.

(51) Int. Cl.
*A61B 17/70* (2006.01)

(52) U.S. Cl.
CPC .................. *A61B 17/7064* (2013.01)

(58) Field of Classification Search
CPC .... A61B 17/7062–17/7071; A61F 2/44; A61F 2/4405; A61F 2/4611
USPC .................................................. 606/246–249
See application file for complete search history.

(56) References Cited

U.S. PATENT DOCUMENTS

| | | | |
|---|---|---|---|
| 6,358,254 B1 * | 3/2002 | Anderson | A61B 17/14 606/103 |
| 6,482,207 B1 * | 11/2002 | Errico | A61B 17/7041 606/264 |
| 6,712,849 B2 * | 3/2004 | Re | A61B 17/1714 606/329 |
| 7,229,448 B2 * | 6/2007 | Goble | A61B 17/1714 606/98 |
| 7,799,057 B2 * | 9/2010 | Hudgins | A61B 17/7064 606/247 |
| 7,935,136 B2 * | 5/2011 | Alamin | A61B 17/842 606/246 |
| 7,951,198 B2 * | 5/2011 | Sucec | A61B 17/562 606/300 |
| 7,988,712 B2 * | 8/2011 | Hale | A61B 17/1671 606/247 |
| 8,070,782 B2 * | 12/2011 | McKay | A61B 17/7064 606/247 |
| 8,231,655 B2 * | 7/2012 | Stinson | A61F 2/4405 606/247 |
| 8,267,966 B2 * | 9/2012 | McCormack | A61B 17/025 606/247 |
| 8,388,659 B1 * | 3/2013 | Lab | A61B 17/7037 606/265 |
| 8,900,270 B2 * | 12/2014 | Fauth | A61B 17/1671 606/247 |

(Continued)

FOREIGN PATENT DOCUMENTS

PA    WO 9848717 A1 * 11/1998 ......... A61B 17/1757

*Primary Examiner* — Eduardo C Robert
*Assistant Examiner* — Michelle C Eckman
(74) *Attorney, Agent, or Firm* — McHale & Slavin, P.A.

(57) ABSTRACT

A facet fixation device formed from an anchor screw and a collet or facet screw that is secured to adjacent pedicles. The anchor screw having an aperture for receipt of a first end of guide wire or polyaxial based facet screw. The collet includes a unidirectional attachment mechanism wherein a wire can be drawn to a desired position to fix the distance between the anchor screw and the collet. Excess wire can then be removed.

8 Claims, 9 Drawing Sheets

(56) References Cited

U.S. PATENT DOCUMENTS

| | | | | |
|---|---|---|---|---|
| 9,017,407 B2* | 4/2015 | Donner | A61F 2/30988 | 623/17.11 |
| 9,078,701 B2* | 7/2015 | Thalgott | A61B 17/70 | |
| 2003/0060825 A1* | 3/2003 | Alfaro | A61F 2/446 | 623/17.11 |
| 2003/0149436 A1* | 8/2003 | McDowell | A61B 17/68 | 606/916 |
| 2004/0116927 A1* | 6/2004 | Graf | A61F 2/4405 | 606/247 |
| 2004/0127906 A1* | 7/2004 | Culbert | A61B 17/7064 | 606/247 |
| 2004/0230201 A1* | 11/2004 | Yuan | A61B 17/1757 | 606/99 |
| 2004/0230304 A1* | 11/2004 | Yuan | A61B 17/1757 | 623/17.11 |
| 2005/0055096 A1* | 3/2005 | Serhan | A61F 2/08 | 623/17.11 |
| 2005/0131406 A1* | 6/2005 | Reiley | A61B 17/7064 | 606/247 |
| 2005/0143818 A1* | 6/2005 | Yuan | A61B 17/1757 | 623/17.11 |
| 2005/0149030 A1* | 7/2005 | Serhan | A61B 17/7064 | 606/247 |
| 2005/0159746 A1* | 7/2005 | Grob | A61B 17/1757 | 606/247 |
| 2005/0240264 A1* | 10/2005 | Tokish | A61B 17/7064 | 623/17.11 |
| 2006/0058788 A1* | 3/2006 | Hammer | A61B 17/7034 | 606/266 |
| 2006/0190081 A1* | 8/2006 | Kraus | A61B 17/7064 | 623/17.11 |
| 2006/0235391 A1* | 10/2006 | Sutterlin, III | A61B 17/7064 | 606/86 A |
| 2007/0055373 A1* | 3/2007 | Hudgins | A61B 17/7064 | 623/17.11 |
| 2007/0088358 A1* | 4/2007 | Yuan | A61F 2/4405 | 606/279 |
| 2007/0118118 A1* | 5/2007 | Kwak | A61B 17/7032 | 606/279 |
| 2007/0162026 A1* | 7/2007 | Tipirneni | A61B 17/68 | 606/916 |
| 2007/0233092 A1* | 10/2007 | Falahee | A61B 17/7064 | 606/279 |
| 2007/0233256 A1* | 10/2007 | Ohrt | A61F 2/4405 | 623/17.11 |
| 2007/0270967 A1* | 11/2007 | Fallin | A61F 2/4405 | 623/17.11 |
| 2008/0086131 A1* | 4/2008 | Daly | A61B 17/7032 | 606/264 |
| 2008/0147126 A1* | 6/2008 | Tipirneni | A61B 17/8869 | 606/300 |
| 2008/0147127 A1* | 6/2008 | Tipirneni | A61B 17/742 | 606/301 |
| 2008/0177335 A1* | 7/2008 | Melkent | A61B 17/7001 | 606/309 |
| 2008/0255618 A1* | 10/2008 | Fisher | A61B 17/7064 | 606/247 |
| 2008/0255622 A1* | 10/2008 | Mickiewicz | A61B 17/7064 | 606/319 |
| 2008/0255666 A1* | 10/2008 | Fisher | A61B 17/7064 | 623/17.16 |
| 2009/0157119 A1* | 6/2009 | Hale | A61B 17/1659 | 606/247 |
| 2009/0192551 A1* | 7/2009 | Cianfrani | A61B 17/686 | 606/301 |
| 2009/0204152 A1* | 8/2009 | Blain | A61F 2/442 | 606/249 |
| 2009/0264928 A1* | 10/2009 | Blain | A61B 17/7064 | 606/247 |
| 2009/0270917 A1* | 10/2009 | Boehm | A61B 17/7023 | 606/246 |
| 2009/0306718 A1* | 12/2009 | Tipirneni | A61B 17/92 | 606/263 |
| 2009/0312798 A1* | 12/2009 | Varela | A61B 17/7064 | 606/247 |
| 2009/0312804 A1* | 12/2009 | Gamache | A61B 17/704 | 606/308 |
| 2010/0030267 A1* | 2/2010 | Winslow | A61B 17/7005 | 606/246 |
| 2010/0069969 A1* | 3/2010 | Ampuero | A61B 17/8605 | 606/301 |
| 2010/0082065 A1* | 4/2010 | Butler | A61B 17/7064 | 606/247 |
| 2010/0094356 A1* | 4/2010 | Varela | A61B 17/862 | 606/304 |
| 2010/0185239 A1* | 7/2010 | Patel | A61B 17/7071 | 606/246 |
| 2010/0191286 A1* | 7/2010 | Butler | A61B 17/7064 | 606/247 |
| 2010/0204700 A1* | 8/2010 | Falahee | A61B 17/7064 | 606/80 |
| 2010/0234893 A1* | 9/2010 | Iott | A61B 17/7041 | 606/278 |
| 2010/0241164 A1* | 9/2010 | Fischer | A61B 17/683 | 606/247 |
| 2010/0305700 A1* | 12/2010 | Ben-Arye | A61B 17/70 | 623/17.11 |
| 2010/0312280 A1* | 12/2010 | Overes | A61B 17/68 | 606/264 |
| 2011/0060366 A1* | 3/2011 | Heim | A61B 17/562 | 606/247 |
| 2011/0160772 A1* | 6/2011 | Arcenio | A61B 17/7053 | 606/248 |
| 2011/0182693 A1* | 7/2011 | Helgerson | A61B 17/7064 | 411/337 |
| 2011/0184470 A1* | 7/2011 | Gorek | A61B 17/7011 | 606/279 |
| 2011/0184519 A1* | 7/2011 | Trieu | A61B 17/7076 | 623/17.11 |
| 2011/0190821 A1* | 8/2011 | Chin | A61B 17/8685 | 606/264 |
| 2011/0288588 A1* | 11/2011 | Chin | A61B 17/7064 | 606/247 |
| 2011/0313466 A1* | 12/2011 | Butler | A61B 17/7064 | 606/279 |
| 2011/0313472 A1* | 12/2011 | Yap | A61B 17/7064 | 606/305 |
| 2011/0319925 A1* | 12/2011 | Helgerson | A61B 17/3421 | 606/198 |
| 2012/0095509 A1* | 4/2012 | Jensen | A61B 17/686 | 606/248 |
| 2012/0095560 A1* | 4/2012 | Donner | A61F 2/30988 | 623/17.11 |
| 2012/0116454 A1* | 5/2012 | Edidin | A61B 17/1757 | 606/247 |
| 2012/0165871 A1* | 6/2012 | Malone | A61B 17/7064 | 606/247 |
| 2012/0221048 A1* | 8/2012 | Blain | A61B 17/82 | 606/247 |
| 2012/0221049 A1* | 8/2012 | Blain | A61B 17/7053 | 606/247 |
| 2012/0226325 A1* | 9/2012 | Lyons | A61B 17/7064 | 606/305 |
| 2012/0277874 A1* | 11/2012 | Yuan | A61L 27/56 | 623/17.16 |
| 2012/0283776 A1* | 11/2012 | Mishra | A61B 17/7064 | 606/247 |
| 2013/0012994 A1* | 1/2013 | McCormack | A61B 17/025 | 606/247 |
| 2013/0018427 A1* | 1/2013 | Pham | A61B 17/7055 | 606/301 |
| 2013/0123848 A1* | 5/2013 | Duggal | A61B 17/8695 | 606/247 |
| 2013/0144343 A1* | 6/2013 | Arnett | A61B 17/70 | 606/279 |
| 2013/0197585 A1* | 8/2013 | Jackson | A61B 17/7035 | 606/278 |

(56) References Cited

U.S. PATENT DOCUMENTS

| | | | |
|---|---|---|---|
| 2013/0226239 A1* | 8/2013 | Altarac | A61B 17/7064 606/247 |
| 2014/0012318 A1* | 1/2014 | Goel | A61B 17/7064 606/247 |
| 2014/0025113 A1* | 1/2014 | McCormack | A61F 2/4405 606/247 |
| 2014/0088707 A1* | 3/2014 | Donner | A61B 17/68 623/17.11 |
| 2014/0188223 A1* | 7/2014 | Jensen | A61F 2/44 623/17.11 |
| 2014/0200618 A1* | 7/2014 | Donner | A61B 17/1757 606/281 |
| 2014/0243828 A1* | 8/2014 | Heiney | A61B 17/8085 606/70 |
| 2014/0277141 A1* | 9/2014 | Baynham | A61F 2/4405 606/247 |
| 2014/0277188 A1* | 9/2014 | Poulos | A61B 17/1655 606/304 |
| 2014/0277196 A1* | 9/2014 | Foley | A61B 17/7076 606/86 A |
| 2014/0277209 A1* | 9/2014 | Arthur | A61B 17/8816 606/86 R |
| 2014/0277210 A1* | 9/2014 | Arthur | A61B 17/8819 606/86 R |
| 2014/0288601 A1* | 9/2014 | Baynham | A61B 17/7064 606/247 |
| 2014/0296916 A1* | 10/2014 | McCormack | A61B 17/025 606/247 |
| 2015/0025575 A1* | 1/2015 | Kleiner | A61B 17/025 606/247 |
| 2015/0094766 A1* | 4/2015 | Blain | A61B 17/82 606/247 |
| 2015/0094767 A1* | 4/2015 | Blain | A61B 17/7064 606/247 |

* cited by examiner

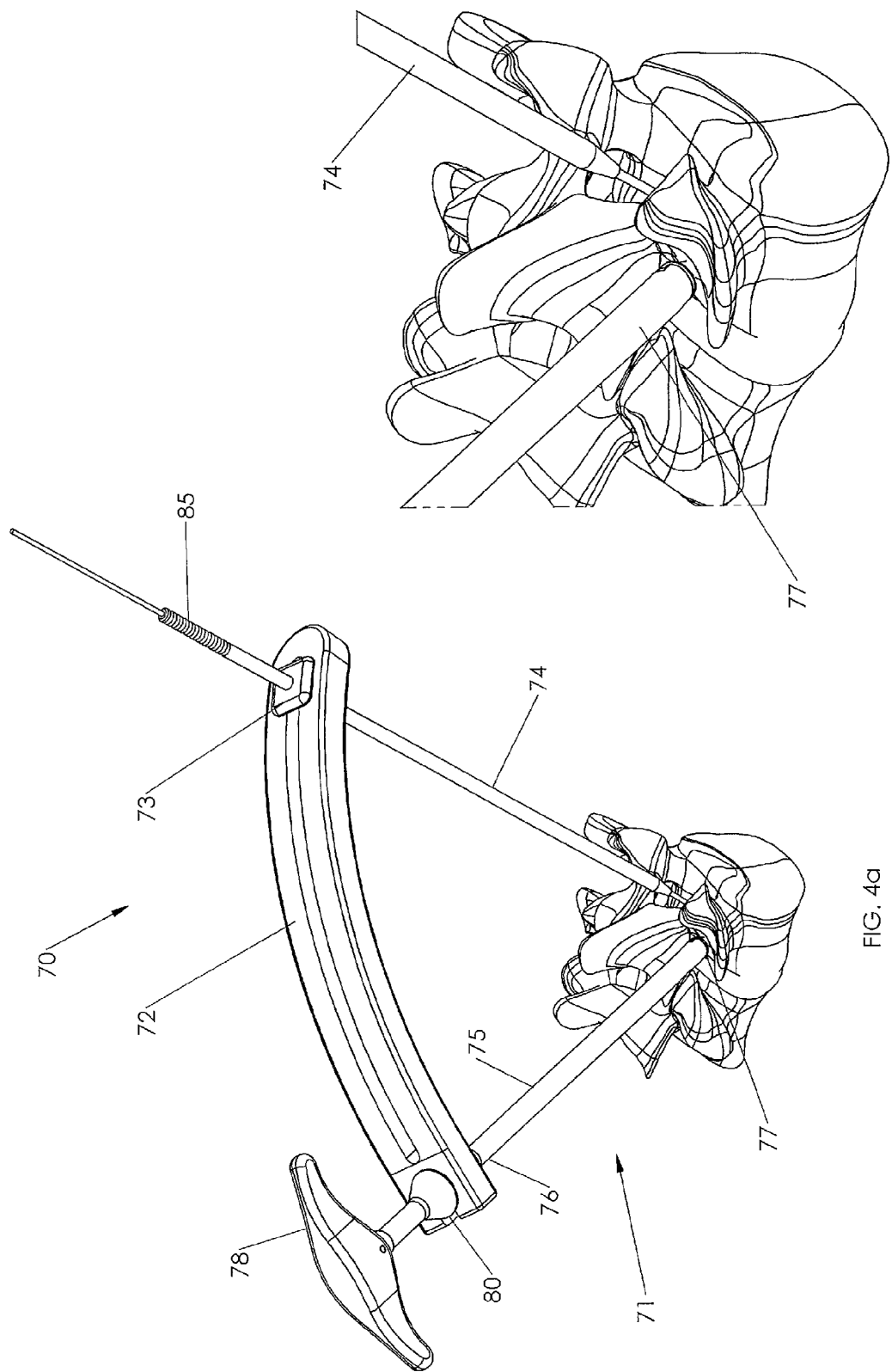

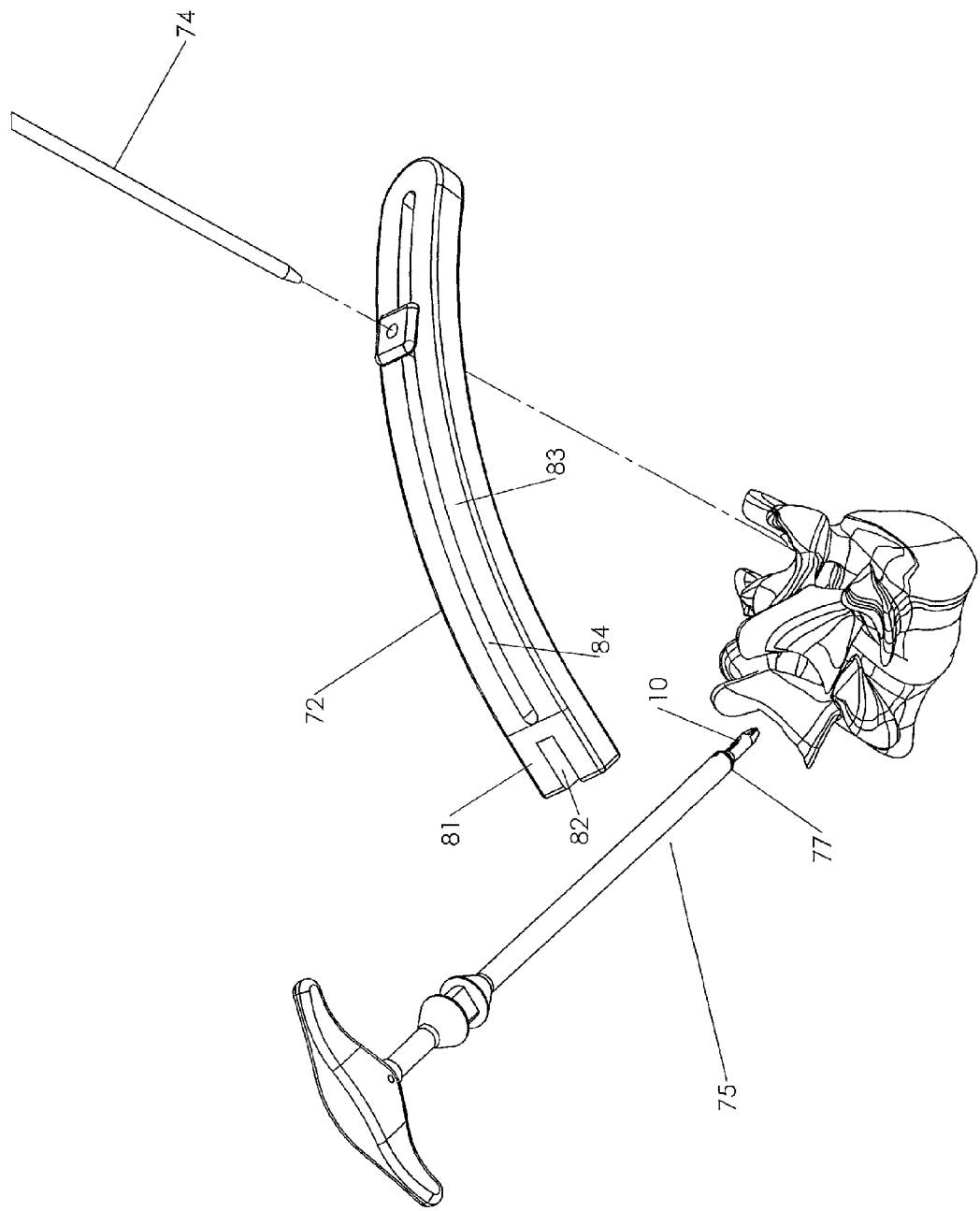

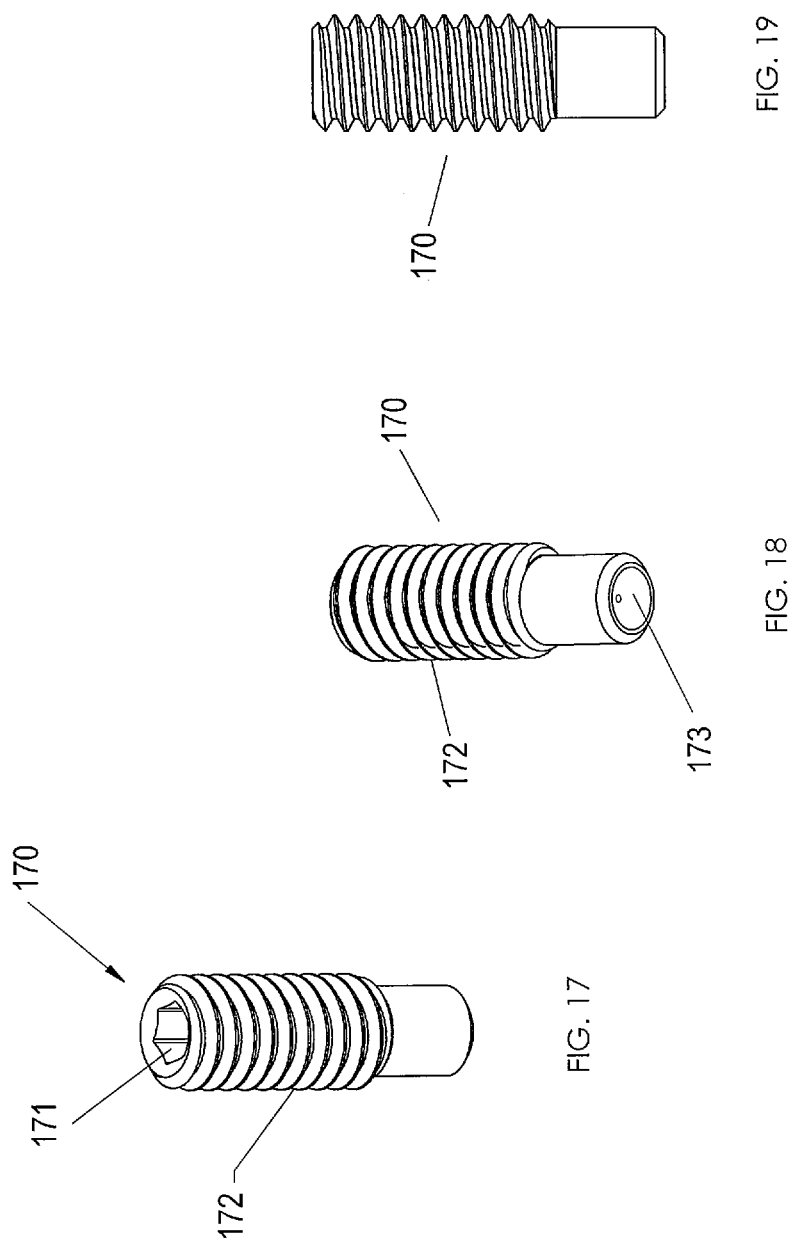

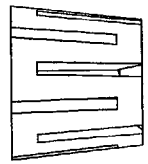
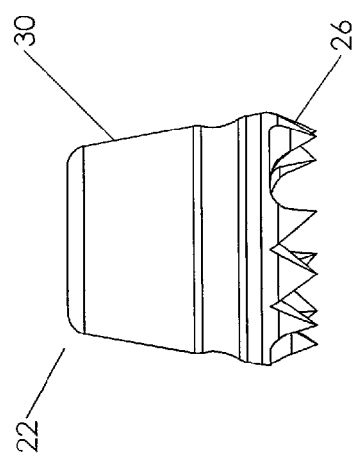
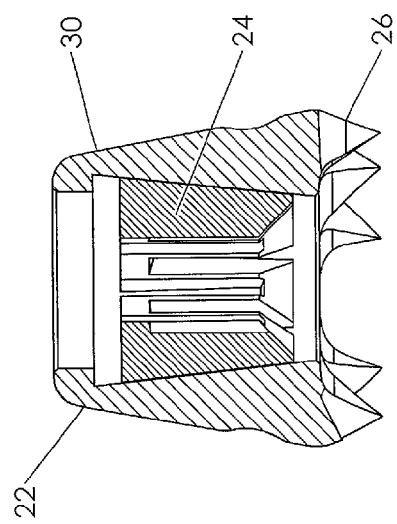

FACET FIXATION WITH ANCHOR WIRE

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/785,369 filed on Mar. 14, 2013, entitled "Facet Fixation with Anchor Wire," the contents of which are hereby expressly incorporated herein by reference. The application is related to U.S. patent application Ser. No. 14/210,227, which claims the priority of U.S. Provisional Patent Application Ser. No. 61/784,465 entitled "Pedicle-based Construct Facet Joint Fixation Device" the contents of which are expressly incorporated herein by reference.

FIELD OF THE INVENTION

The present invention relates generally to surgically-implantable spinal devices and, more specifically, to a facet joint fixation device.

BACKGROUND OF THE INVENTION

It is often desirable to stabilize/immobilize one or more facet joints of the spine of a patient in the treatment of various spinal ailments/defects. Facet arthrodesis is used to fuse a facet joint including a superior facet and an inferior facet in spinal treatment operations.

There are numerous implants and associated methods for performing stabilization/immobilization. Conventional implants are bone screws that are threaded through the superior and inferior facets to immobilize the facet joint so as to permit the adjoined bone sections to fuse together.

Screws are the most common device used for facet fixation. Unfortunately, a facet screw can loosen, fracture and may be difficult to gain the trajectory required for optimal placement.

SUMMARY OF THE INVENTION

Disclosed is a facet fixation device formed from an anchor screw that is secured to a pedicle. A wire is secured to the anchor screw and drawn through an adjacent pedicle and attached thereto by use of a collet assembly. The collet assembly includes a unidirectional attachment wherein the wire can be drawn to a desired position. Excess wire can then be removed.

In an alternative embodiment a threaded screw can be used in combination with the wire; the threaded screw having a cannulised shape allowing the screw to use the wire as a guide as it is drawn to the anchor screw.

An objective of the invention is to provide a facet securement system that serves as a platform for dynamic stabilization as well as motion preservation.

Another objective of the invention is to provide a minimally invasive, cost effective alternative to pedicle screw fixation for posterior facet fusions, or as an adjunct to an anterior or lateral inter-body fusion.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 4A is a pictorial representation showing an embodiment of a guiding device;
FIG. 4B is a pictorial representation of the guiding device;
FIG. 4C is a pictorial representation of the guiding device;
FIG. 17 is a top perspective view of a set screw;
FIG. 18 is a bottom perspective view of the set screw;
FIG. 19 is a side view of the set screw;
FIG. 20 is a side view of a locking assembly;
FIG. 21 is a side view of a retention collet assembly;
FIG. 22 is cross sectional side view of FIG. 20.

DETAILED DESCRIPTION OF THE INVENTION

Figure 1:
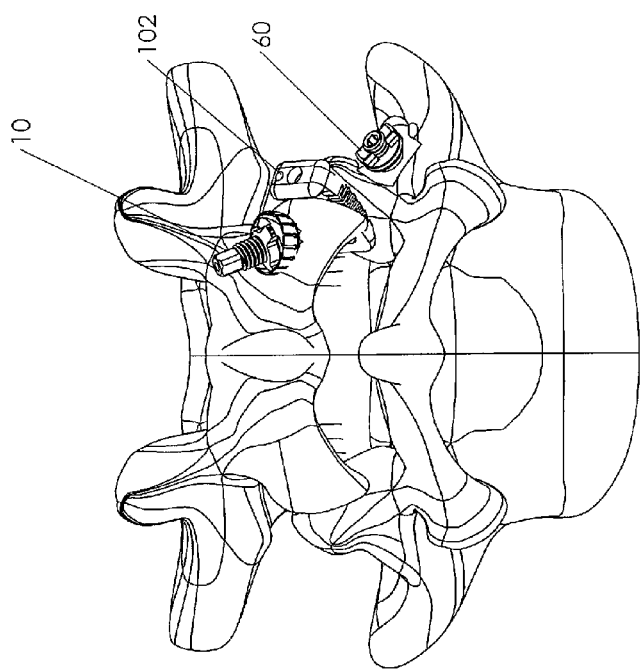
FIG. 1 is a pictorial representation showing a facet system implanted in adjacent vertebrae.

The medical device embodied herein provides a better overall approach to modifying the relationship between adjacent vertebral bodies without altering the surrounding anatomy, thereby reducing the time a patient and surgeon have to spend in surgery, and reducing or altogether eliminating hospitalization following the procedure.

Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions: The terminology used herein is for the purpose of describing particular embodiments only and is not intended to be limiting of the invention. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The following description of the preferred embodiments is merely exemplary in nature and is in no way intended to limit the invention, its application or uses.

Now referring to FIGS. 1-3 and 5-23 which set forth the facet system of the instant invention. The facet fixation device is formed from an anchor screw 10 that can be threaded, or otherwise constructed and arranged for securement of a flexible wedge shaped implant 102 to a pedicle 100. The anchor screw 10 is formed from a body 12 that is hollow along at least a portion of the length for the threadable receipt of a set screw 14.

The body 12 includes a slot aperture 16 along a length of the screw for receipt of a first end of a wire 20. A hole is drilled through an adjacent pedicle, and the wire is drawn through the adjacent pedicle and placed into or through the slot aperture 16. An upper end 18 of the body 12 includes engagement tabs 19 to allow for ease of installation.

A collet assembly 22 is placed over a second end of the wire 20 and drawn to the anchor screw 10 until a desired distance between the members is obtained. The collet assembly 22 includes an internal segmented band or wire retention collet constructed and arranged to grasp the wire 20 in a unidirectional manner. Teeth 26 placed along a lower end of the collet assembly 22 prevent rotation by attachment to the bone. Excess wire can then be removed. The bone is decorticated to stimulate bone growth and increase the potential for fusion of the vertebrae.

Figure 3:
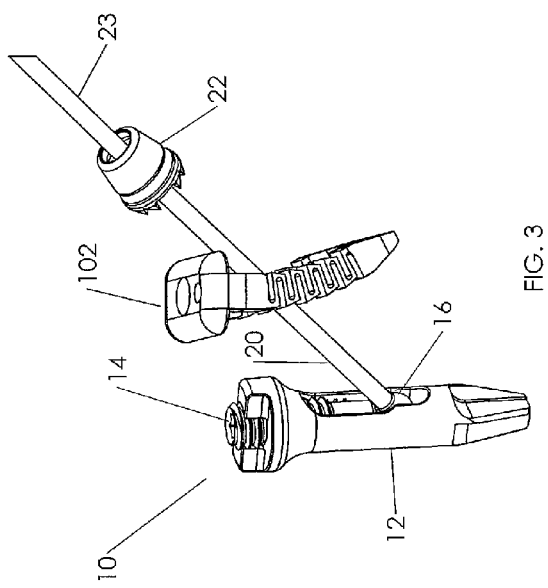
FIG. 3 is a schematic representation showing an embodiment of a facet system.
Figure 2:
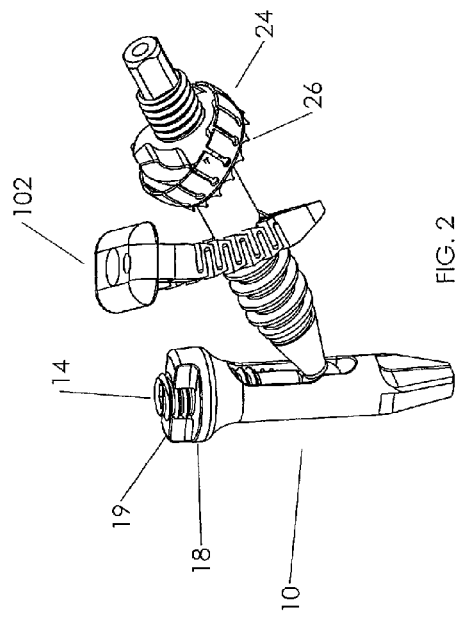
FIG. 2 is a pictorial representation showing an embodiment of a facet system.
Figure 7:
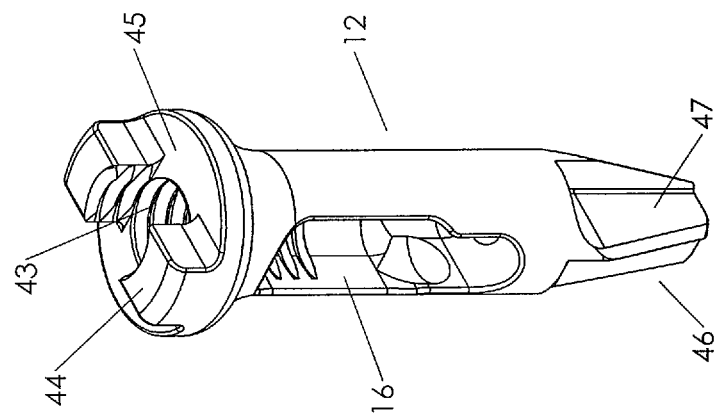
FIG. 7 is a perspective view of FIG. 5.
Figure 6:
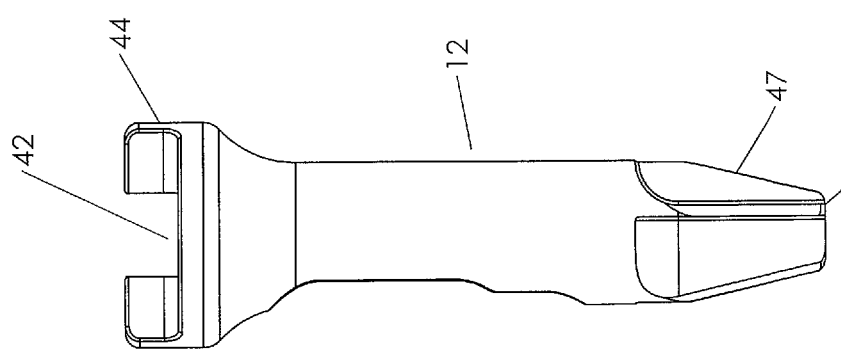
FIG. 6 is a side view of FIG. 5.
Figure 5:
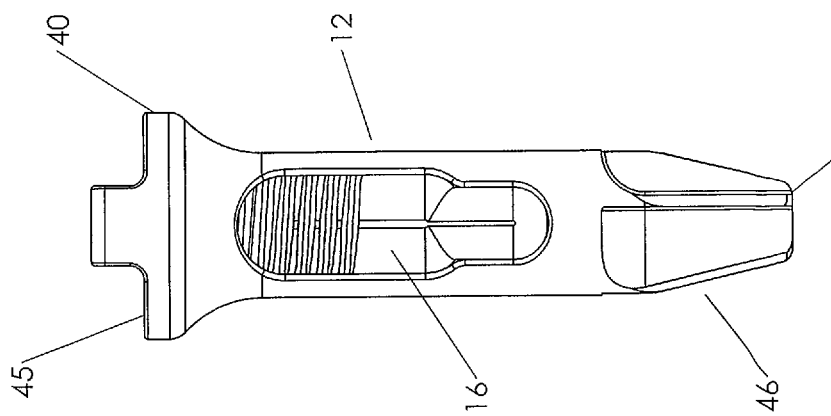
FIG. 5 is a front view of the anchor screw.

Having provided an overview of a facet system, various embodiments are now discussed. In preferred embodiments, a facet fixation device comprises an anchor screw 10, a wire 20, a locking member or locking assembly 22 (FIGS. 1, 2 and 3). The anchor screw 10 comprises a hollow body 12, an aperture 16, a first end 40, and a second end 41 (FIGS. 5, 6 and 7). The first end 40 of the anchor screw 10 comprises an aperture having threads 43 for receiving a set screw, and at least one engagement tab 44 disposed on a shoulder 45. The first end 40 can engage a pedicle anchor drive, or set screw. The second end comprises an anchor 46, wherein the anchor comprises a fluted shaped end; alternatively, a threaded end, a twist bit shaped end, or combinations thereof may be used. Preferably, the anchor is a flute shaped end 47.

In preferred embodiments, the hollow body 12 extends along at least a portion of the anchor screw length for threadably receiving a set screw. The hollow body 12 comprises an aperture 16 for receipt of the wire 20 or a wire guide 23.

In preferred embodiments, the locking member or locking assembly 22 comprises a housing body 30 and a wire retention collet 24, wherein the housing body 30 comprises teeth 26 or other gripping members disposed on the lower part of the housing body for attachment to bone (FIGS. 21, 22 and 23). The wire is spooled or drawn by the wire retention collet assembly, thereby tightening the wire and drawing or immobilizing the vertebrae.

The wire can be tightened and drawn by a gripping floating washer 50, wherein the gripping floating washer (FIGS. 10-16) comprises a floating washer 51, the floating washer comprising a pocket 52 dimensioned to receive a retention nut 53, the pocket having at least one expansion slot 54 on the upper end of the floating washer 51; anchoring teeth 55 disposed on the lower end of the floating washer 51, which are shaped and sized for attachment to the vertebra. As used herein, the term "floating" with respect to the washer means that the washer can accommodate varying sizes of retention nuts. In the preferred embodiment the retention nut 53 includes extension tabs 57 to engage the expansion slots 54 of the floating washer 50. The extension tabs 57 provide a frictional engagement between the retention nut 53 and the floating washer to prevent the retention nut from rotation until the frictional engagement with the expansion slots 54 is overcome.

In preferred embodiments, the retention nut 53 comprises one or more axes 56 for engaging a facet screw. In alternative embodiments, the floating washer 50 comprises threads or a groove for engaging a housing body and the housing body comprises threads or grooves to engage the floating washer.

Figure 9:
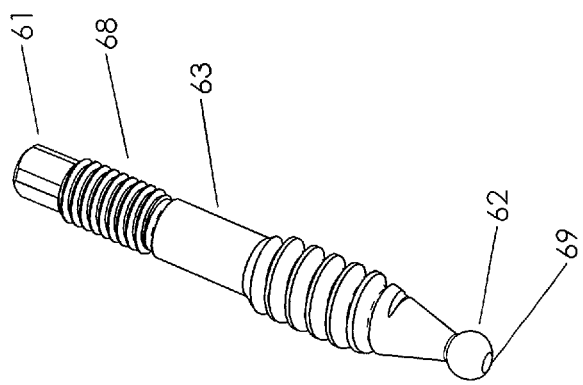
FIG. 9 is a perspective view of FIG. 8.
Figure 8:
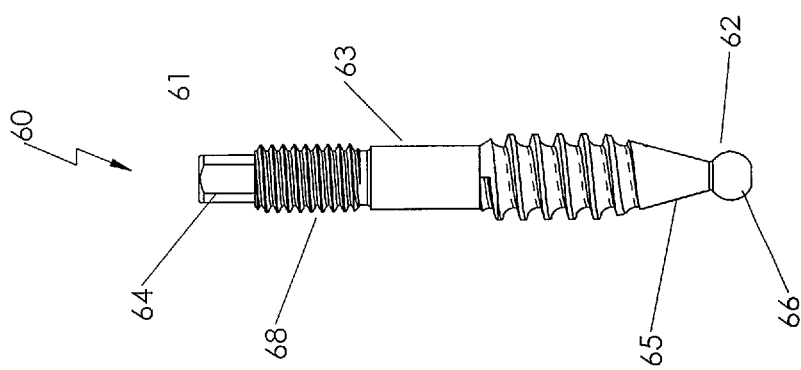
FIG. 8 is front view of a facet screw.
Figure 13:
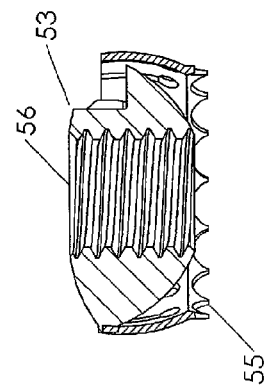
FIG. 13 is a cross sectional view of FIG. 13.
Figure 11:
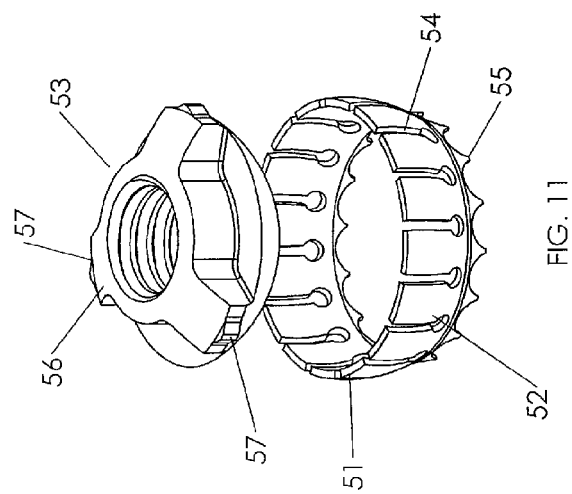
FIG. 11 is a representation of a retention nut and floating washer showing each unit separately.
Figure 10:
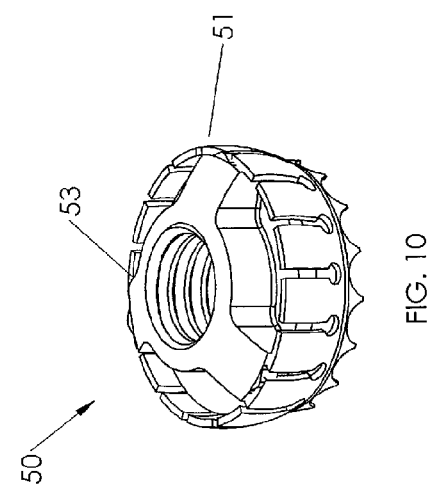
FIG. 10 is a representation of a retention nut and floating washer.
Figure 12:
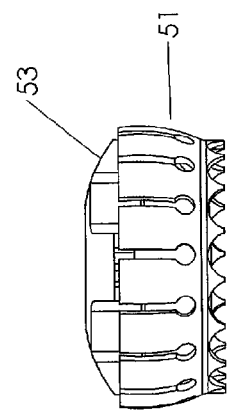
FIG. 12 is a side view FIG. 10.
Figure 15:
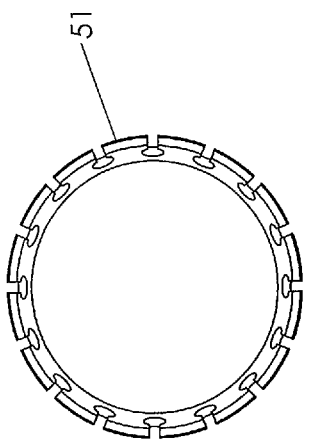
FIG. 15 is top view of the floating washer.
Figure 16:
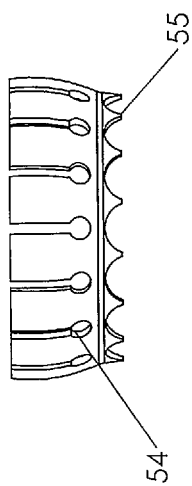
FIG. 16 is side view of FIG. 15.
Figure 14:
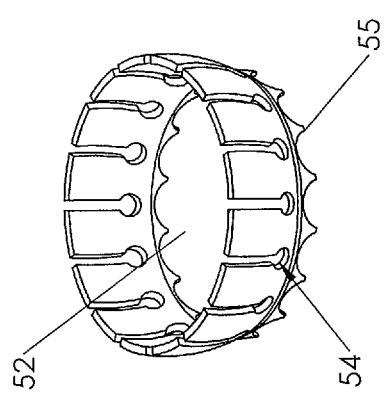
FIG. 14 is a representation of a floating washer.

The facet fixation device comprises a facet screw 60 (FIGS. 8 and 9). The facet screw 60 can be inserted in the aperture 16 of the anchor screw 10 as shown in FIG. 2. The facet screw comprises a first end 61 and a second end 62, the first end and second end connected by a body 63, wherein the first end comprises a facet screw driving member 64 and the second end 62 comprises a tapered end 65 and a retention tip 66 wherein the retention tip is bulbous, spherical or comprises one or more axes. In preferred embodiments, the retention tip 66 is cannulated 69.

The body 63 of the facet screw 60 comprises threading on the upper portion proximal to the first end 61 for retention of a nut; a central smooth section 63; threading 68 proximal to the second end 62 for anchoring into the vertebra.

In this embodiment, the facet fixation device comprises a set screw 170 (FIGS. 17, 18, 19) comprises a set screw driving member 171, threading 172 for at least a portion of the length of the anchor screw, and a polyaxial capture cup 173 at an end distal to capture the polyaxial ball at the end of the wire.

In a preferred embodiment, a guiding device 70 comprises a pedicle anchor driver 71, a targeting guide 72, a guide bushing 73, and guide wire tube 74. In other embodiments, a guiding device is provided. FIGS. 4A, 4B and 4C are schematic representations of an embodiment of a guiding device 70 for use, if desired, in the angular positioning of the facet system for installation. The pedicle anchor driver 71 comprises a body portion 75 having a first end 76 for engaging a driving member 78 and a second end 77 for engaging a pedicle anchor screw.

In the preferred embodiment, the driving member 78 comprises a handle or actuating member 79 at a first end for driving the pedicle anchor driver, and an engaging member 80 for engaging the pedicle anchor driver 71. The engaging member 80 comprises threads, tabs, grooves, or axial protuberances, dimensioned and patterned for engaging the first end 76 of the pedicle anchor driver 71 and the targeting guide 72. The second end 77 of the pedicle anchor driver 71 comprises threads, tabs, grooves, or axial protuberances, dimensioned and patterned for engaging the pedicle anchor screw 10 (FIG. 4C).

In the preferred embodiment, a flexible wedge-shaped implant is positioned between adjacent vertebrae; the flexible wedge-shaped implant comprising an insert end, an outer end, wherein the insert end and the outer end are spaced apart by a first and a second side member, each side member having one or more recesses defining a hinge structure and providing flexibility. The insert end comprises a tapered end for ease of inserting the device in between adjacent vertebrae. The targeting guide 72 comprises an end 81 having an aperture 82 for receiving the pedicle anchor driver 71, an elongated body member 83 having a central opening 84 running along the length of the elongated body 83, a guide bushing 73 for positioning and maintaining the positioning of a guide wire hollow body or tube having threading 85 at an end distal to a vertebra. The targeting guide comprises a flat or curving elongated body member.

The system cooperates as a method of stabilizing or immobilizing vertebrae in a patient comprises inserting the anchor screw 10 in a pedicle; drilling a hole through an adjacent pedicle; inserting a wire through the hole and drawing the wire through to an adjacent pedicle, threading the anchor screw with the wire into or through an aperture in the anchor screw; drawing the thread to alter the distance between the vertebrae; locking and immobilizing the wire with a locking member or floating washer, thereby stabilizing or immobilizing vertebrae in a patient. See, for example, FIG. 1. If desired, a spacer, see, for example, FIGS. 2 and 3, is optionally inserted between the vertebrae for accessing the pedicles.

In other preferred embodiments, kits are provided. In one embodiment, a kit comprises a facet fixation device and/or a guiding device. The kit comprises one or more components of a facet fixation device embodied herein. In one embodiment, a kit comprises an anchor screw 10, a wire 20, a locking member, a locking assembly, a wire retention collet, a floating washer, a facet screw, a set screw, a pedicle anchor driver, a targeting guide, a guide bushing, a guide wire or combinations thereof.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A facet fixation system comprising: an anchor having a first end, a second end, and a main body having a length, said main body being hollow along at least a portion of said length and having a slotted aperture along said length, said slotted aperture positioned between said first end and said second end, a set screw having threads for moving a polyaxial capture cup formed in said set screw along the length of said slotted aperture; a facet screw having a polyaxial shaped first end constructed and arranged for securement in said slotted aperture by said set screw and a second end having a floating washer defined by an inner surface and an outer surface, said inner surface forming a pocket to receive a threaded retention nut allowing angular engagement of said floating washer to said facet screw, said outer surface including anchoring teeth for frictional securement to bone, said facet screw is cannulated for receipt of a guide wire wherein said facet screw is slidably positioned along a length of said guide wire for placement with said anchor; wherein said anchor is configured to be mounted to vertebrae bone and said facet screw is configured to be placed in adjacent vertebrae bone to capture a flexible wedge shaped facet spacer therebetween.

2. The facet fixation system according to claim 1 wherein said guide wire is coupled to said anchor screw wherein said facet screw is constructed and arranged to be drawn toward said anchor screw before securement.

3. The facet fixation system according to claim 1 wherein said threaded retention nut has a curved lower surface dimensioned for placement within a curved inner surface of said floating washer whereby said retention nut comprises one or more axes for engaging the floating washer.

4. The facet fixation system according to claim 1 wherein said floating washer has a plurality of expansion slots for locking engagement with extension tabs positioned on said retention nut.

5. The facet fixation system according to claim 1 wherein said facet screw include anchoring teeth disposed on a lower end, which are shaped and sized for attachment to the vertebra.

6. The facet fixation system according to claim 1 wherein said facet screw includes a central section constructed and arranged to engage a facet spacer.

7. The facet fixation system according to claim 1 wherein said anchor screw comprises an aperture having threads for receiving said set screw and at least one engagement tab disposed on a shoulder for guiding a set screw.

8. The facet fixation system according to claim 1 wherein said anchor screw includes a fluted shaped end.

* * * * *